US007507225B2

(12) United States Patent
Mizutani et al.

(10) Patent No.: US 7,507,225 B2
(45) Date of Patent: Mar. 24, 2009

(54) INTERLABIAL PAD

(75) Inventors: Satoshi Mizutani, Kagawa (JP); Wataru Yoshimasa, Kagawa (JP); Yuki Noda, Kagawa (JP)

(73) Assignee: Uni-Charm Corporation, Shikokuchuo-Shi, Ehime-Ken (JP)

( * ) Notice: Subject to any disclaimer, the term of this patent is extended or adjusted under 35 U.S.C. 154(b) by 294 days.

(21) Appl. No.: 11/007,590

(22) Filed: Dec. 8, 2004

(65) Prior Publication Data
US 2005/0137559 A1 Jun. 23, 2005

(30) Foreign Application Priority Data
Dec. 9, 2003 (JP) ............... 2003-411093

(51) Int. Cl.
*A61F 13/15* (2006.01)
*A61F 13/20* (2006.01)
(52) U.S. Cl. ............ 604/385.17; 604/367; 604/904
(58) Field of Classification Search ..............
604/385.17–385.18, 904, 367–375, 378,
604/385.01, 11
See application file for complete search history.

(56) References Cited
U.S. PATENT DOCUMENTS
5,762,644 A * 6/1998 Osborn et al. .......... 604/385.17
6,033,391 A 3/2000 Osborne, III et al.
6,254,584 B1 * 7/2001 Osborn et al. .......... 604/385.17
7,307,197 B2 * 12/2007 Mizutani et al. ............ 604/367
2004/0147893 A1 * 7/2004 Mizutani et al. ....... 604/385.17

FOREIGN PATENT DOCUMENTS
JP 11-500341 A 1/1999
JP 2001-474 A 1/2001
WO WO-02/094153 A1 11/2002
WO WO-02/094155 A1 11/2002
WO 2004/024050 * 3/2004

OTHER PUBLICATIONS
Patent Abstracts of Japan for 2001-000474 published on Jan. 9, 2001.
Abstarct of WO 97/18784 (JP 11-500341) published on May 29, 1997.

* cited by examiner

*Primary Examiner*—Michele Kidwell
(74) *Attorney, Agent, or Firm*—Darby & Darby P.C.

(57) ABSTRACT

It is an object of the present invention to provide an interlabial pad, with which anisotropy is provided in regard to the degree of freedom of the surface side sheet that forms the face that contacts the labia of a wearer, so that the interlabial pad will not fall off readily. An interlabial pad 20, fitted on by being sandwiched partially or wholly between labia, the interlabial pad 20 comprising: a vestibular floor contacting region 22A, contacting a vestibular floor of a wearer, and an inner wall contacting region 22B, contacting a inner walls of the labia of the wearer; the degree of freedom of the respective fibers that form the vestibular floor contacting region 22A is adjusted to be higher than the degree of freedom of the fibers that form the inner wall contacting region 22B.

22 Claims, 4 Drawing Sheets

INTERLABIAL PAD

CROSS-REFERENCE TO RELATED APPLICATIONS

This application is based upon and claims the benefit of priority from Japanese Patent application No. 2003-411093 filed on Dec. 9, 2003, the entire contents of which is incorporated herein by reference.

FIELD OF THE INVENTION

The present invention concerns an interlabial pad to be fitted between the labia of a woman, and to be more detailed, concerns an interlabial pad with an arrangement that provides good fitting comfort and safety.

RELATED ART

Conventionally, interlabial pads, which are used by being sandwiched between the labia of women, have been known as menstrual products for women (see Patent Document 1). Since such an interlabial pad is fitted on by a part thereof being sandwiched between the labia, it is put in highly close contact with a body and does not give rise readily to leakage of menstrual blood, etc., in comparison to a menstrual napkin. An interlabial pad also provides the merit of being low in psychological reluctance during fitting in comparison to a tampon, which is inserted inside the vagina. Meanwhile, since an interlabial pad is fitted onto a body by the sandwiching force of the labia, the interlabial pad must flexibly follow the movements of the left and right labia that result from movements of the wearer. If it is difficult for an interlabial pad to follow body movements, there is a high possibility that the interlabial pad will fall off from the labia of a wearer. Thus various interlabial pads that can be put in closer contact with the body during fitting have been examined (see Patent Document 2).

The interlabial pad disclosed in Patent Document 1 has a substantially elliptical shape with protrusions disposed on a face at substantially the centers in the longitudinal direction of a cover member, disposed on a face that is opposite to the other face contacting the labia. A wearer first pinches the protrusions and can then fit the interlabial pad so as to be close contact with the interior of the labia in a state were the interlabial pad is folded in two along the central part in the longitudinal direction as the axis with the face of the interlabial pad that comes in contact with the labia to be outer side.

The interlabial pad described in Patent Document 2 has a pair of flexible absorbent extensions, which can maintain the state of contact with the inner labial walls of a wearer during fitting, provided at a part of an absorbent and has a biocompatible adhesive agent applied to the sides of these flexible extensions that face the inner labial walls. Fall-off of the interlabial pad due to actions of a wearer can be prevented by the flexible extensions that are coated with the biocompatible adhesive agent.

[Patent Document 1] Japanese Translation of International Application No. H-11-500341

[Patent Document 2] U.S. Pat. No. 6,033,391 Specification

However, neither the interlabial pad disclosed in Patent Document 1 nor that disclosed in Patent Document 2 take into consideration deformations of the labia due to movements of a wearer. These therefore cannot follow movements of a wearer. Furthermore, with the interlabial pad disclosed in Patent Document 2, since a biocompatible adhesive agent is used, a rash due to irritation may occur depending on the constitution of a wearer. Also, depending on the manner of application of the adhesive agent, the body fluid permeation performance of the flexible extensions may drop and menstrual blood may flow out without becoming absorbed by the main body of the absorbent body.

The present invention has been made in view of the above issues and an object thereof is to provide an interlabial pad of favorable fitting comfort by making the interlabial pad be able to follow deformations of the labia that accompany movements of a wearer.

SUMMARY OF THE INVENTION

In order to achieve the above object, the present invention provides an interlabial pad, with which regions that can follow movements of the labia of a wearer in the fitted state are provided by adjustment of the fiber distribution at parts of the interlabial pad that contact the labia.

The present invention specifically provides the following:

(1) An interlabial pad, fitted on by being sandwiched partially or wholly between labia; wherein the interlabial pad comprises an inner wall contacting region contacting the inner walls of the labia of a wearer in a fitted state, and a vestibular floor contacting region contacting the vestibular floor of the wearer in the fitted state; and wherein the vestibular floor contacting region is provided with ease of deformation so as to enable the inner wall contacting region to follow variations of the shape of the interior of the labia that arise accompanied by movements of the wearer.

With the present invention of (1), by providing the vestibular floor contacting region with ease of deformation, the compliance of the vestibular floor contacting region is adjusted to be higher than the compliance of the inner wall contacting region. Thus in the fitted state, the vestibular floor contacting region can readily follow movements of the vestibular floor of a wearer. That is, a labial space is formed by the left and right labia and the extremely delicate and hypersensitive vestibular floor, which is surrounded by the labia. Since in accompaniment with the movements of a wearer during walking, the inner labial walls move back and forth in a mutually sliding manner with a central line of the vestibular floor as a symmetry axis, in a state in which an interlabial pad is fitted, friction tends to arise between the inner labial walls and parts of the interlabial pad that contact the inner labial walls. Also during walking, since the left and right labia move back and forth respectively in accompaniment with the movements of the left and right legs of a wearer, in order to accommodate for these movements, the inner labial contacting region must follow the movements of the left and right labia and move largely back and forth. In regard to this point, with the present invention, since the vestibular floor contacting region is provided with ease of deformation, the inner wall contacting region that is positioned to the left and right of the vestibular floor contacting region can readily follow the movements of the inner labial walls. The closely contacting property of the interlabial pad can thus be improved and the interlabial pad will not make a wearer feel a foreign object sensation due to movements of the wearer.

"Vestibular floor" refers to the base part of the left and right labia, that is, the region positioned at the interior of the labia along a line joining the clitoris and the ostium vaginae. "Vestibular floor contacting region" refers to a region of the interlabial pad at which a fiber aggregate contacts the vestibular floor of a wearer. Specifically, a width in the range of 5 mm to 25 mm that spans a longitudinal central axis of the interlabial pad is referred to. Also, "inner wall contacting region" refers to the region of the interlabial pad at which the fiber aggregate contacts the inner walls of the left and right labia of a wearer. Specifically, the region besides the "vestibular floor contacting region" is referred to.

Also, "ease of deformation" refers to the ease of deforming in the manner of straining readily (at low load) in accordance with movements of a wearer, with respect to a reference state wherein the wearer is still with the interlabial pad being fitted. The phrase, "being provided with ease of deformation," means that a change (movement), which gives rise to strain, occurs readily in response to movements of a wearer. Meanwhile, the phrase, "low in ease of deformation," means that a change (movement), which gives rise to strain, does not occur readily in response to movements.

(2) The interlabial pad according to (1), wherein the vestibular floor contacting region has intermittent parts, which can deform in compliance to movements of the wearer, provided on a face that contacts a body of the wearer during fitting.

With the present invention of (2), since the vestibular floor contacting region has intermittent parts provided on the face that contacts a body during fitting, the entire interlabial pad can readily follow movements of the left and right labia of a wearer by the straining of open pores, etc., at the intermittent parts. Close contacting of the interlabial pad is thus improved further and the falling-off of the interlabial pad from the labia of a wearer due to movements of the wearer can be prevented.

Here, "intermittent parts" refer to parts in which slitting or an open pore forming process has been applied. For example, in the case where the interlabial pad comprises an absorbent body, a surface side sheet, which covers the absorbent body and contacts a body, and a back face side sheet, the intermittent parts are provided in the surface side sheet. Specifically in the case of slits, the slits are preferably 1 mm to 20 mm in dimension and 1 to 20 mm in pitch. The slit pattern may be made in the longitudinal direction, lateral direction, diagonal direction, or a combination of these. In regard to an open pore forming process, the open pores are preferably 0.2 mm to 5 mm in diameter and 0.2 mm to 10 mm in pitch. The shape of the open pores is not restricted in particular and may be circular, elliptical, etc.

(3) The interlabial pad according to (1) or (2), wherein the interlabial pad has a practically elongate shape with a longitudinal direction and a lateral direction; wherein the interlabial pad has a sheet at the face that comes in contact with the body of the wearer during fitting; wherein the vestibular floor contacting region of the sheet has a tensile strength in the state of 5% extension in the longitudinal direction of no less than 40 cN/inch and no more than 1000 cN/inch; and the inner wall contacting region of the sheet has a tensile strength in the state of 5% extension of no less than 400 cN/inch and no more than 1500 cN/inch.

With the present invention of (3), by making the tensile strength in the state of 5% extension in the lateral direction of the vestibular floor contacting region lower than the tensile strength of the inner wall contacting region, the interlabial pad can be fitted without making a wearer feel a foreign object sensation. Specifically, by making the tensile strength of the vestibular floor contacting region no less than 40 cN/inch and no more than 1000 cN/inch (1 inch=2.54 cm), the vestibular floor contacting region can be made to follow the inner labial walls of a wearer more readily.

Also, this interlabial pad may contain a fiber aggregate. Here, "fiber aggregate" refers to a lump-like object formed by the gathering together of a plurality of fibers and includes non-woven fabrics and woven fabrics.

With this invention, "tensile strength" refers to the value of stress that is applied to a sample when the sample is extended by 5%. That is, since that the tensile strength is low means that a change (movement) can occur readily in response to a strain due to a movement of a wearer, it is equivalent in meaning to being high in compliance. Methods of adjusting the tensile strength can be largely classified into methods of varying the density of the fiber aggregate at parts and methods of improving the dynamic physical properties of the fibers themselves that make up the fiber aggregate.

As methods of varying the density at parts, the making of the fiber amount of the inner wall contacting region lower than the fiber amount of the vestibular floor contacting region, the use of fibers of large fiber diameter in the vestibular floor contacting region, and the use of heat sealing fibers in the inner wall contacting region, etc., can be cited. The varying of the water jet pressure (making the water jet pressure weak at the vestibular floor contacting region and strong at the inner wall contacting region), varying of the emboss pattern, varying of the embossed area percentage, etc., in the above manufacturing methods can also be cited. Also as methods of improving the dynamic physical properties, methods of providing the vestibular floor contacting region with large amounts of fibers of high crimp percentage or extensibility, split fibers, fibers of low molecular orientation, fibers with lubricant mixed in, fibers that are varied in fiber cross-sectional shape (Y-shape, C-shape, etc.,) and thereby lowered in the area of contact with neighboring fibers, etc., can be cited.

When the tensile strength of the vestibular floor contacting region is less than 40 cN/inch, the fibers slide readily with respect to each other and tend to become fluffed due to friction with the vestibular floor and the possibility of fibers becoming retained becomes high. On the other hand, if the tensile strength is greater than 1000 cN/inch, since the sliding of the fibers with respect to each other will be inadequate, not only will a wearer be made to feel a foreign object sensation, but the hypersensitive clitoris and vicinity thereof may become damaged as well. Also, when the tensile strength of the inner wall contacting region is less than 400 cN/inch, the fibers slide readily with respect to each other and tend to become fluffed due to friction with the vestibular floor and the possibility of fibers becoming retained on the vestibular floor becomes high. On the other hand, if the tensile strength is greater than 1500 cN/inch, since the sliding of the fibers with respect to each other will be inadequate, not only will a wearer be made to feel a foreign object sensation, but the inner labial walls may become damaged as well. The method of measuring the tensile strength shall be described later.

Since by thus setting the 5% extension tensile strength in the longitudinal direction of the vestibular floor contacting region to be no less than 40 cN/inch and no more than 1000 cN/inch, the vestibular floor contacting region can be made to strain readily, the inner wall contacting region can be made to slide back and forth readily in accordance with walking movements of a wearer. That the inner wall contacting region is made to slide back and forth readily by the vestibular floor contacting region of the surface side sheet being made to strain readily shall be illustrated by another measurement method.

That is, the shear rigidity of the surface side sheet with the vestibular floor contacting region as the central axis shall be illustrated.

For the measurement, the Tensile & Shear Tester, made by Kato-Tech Co., Ltd., was used. From the longitudinal direction (MD) and lateral direction (CD) of an interlabial pad, test samples of 10 mm MD×10 mm CD were taken and measurements were made upon mounting each sample so as to shear the sample in the lateral direction and a perpendicular (shearing) direction. In this process, the shear rigidity of KES system (G value) within the shear angle (D value) range of 0° to 5° was read.

The obtained G value is preferably in the range of 1 to 3.5 N/m·degree and more preferably in the range 1.5 to 2.5 N/m·degree. When the G value is no more than 1 N/m·degree, the respective fibers tend to become detached and fluffed and there is a high possibility that fibers will become retained in the labia. On the other hand, if the G value is no less than 3.5 N/m·degree, the vestibular floor contacting region will not be strained readily and the surface side sheet will not follow movements of the labia readily.

(4) The interlabial pad according to any one of (1) to (3), wherein the interlabial pad is equipped with a fiber aggregate on the face that contacts the body during fitting; and in the fiber aggregate, a degree of freedom of respective fibers that form the vestibular floor contacting region is adjusted to be higher than the degree of freedom of the fibers that form the inner wall contacting region.

With the present invention of (4), by adjusting the degree of freedom of the vestibular floor contacting region to be higher than the degree of freedom of the inner wall contacting region, the following of movements of the vestibular floor of a wearer in the fitted state is enabled. However, if the degree of freedom of the inner wall contacting region is made as high as that of the vestibular floor contacting region, the fibers that form the inner wall contacting region will tend to slide with respect to each other and become fluffed due to friction, and the fluffed fibers may become retained on the vestibular floor. In regard to this point, with this invention, since the fibers are mutually made to strain readily by adjusting the degree of freedom of the vestibular floor contacting region to be higher than the degree of freedom of the inner wall contacting region, the interlabial pad can be put in highly close contact and a wearer will not feel a foreign object sensation in accompaniment with movements of the wearer.

Here, "degree of freedom" refers to the ease of following of strain when the fiber aggregate follows movements of a wearer and becomes deformed, with respect to the reference state in which the wearer is still with the interlabial pad being fitted. That the degree of freedom is high means that a large portion of the fibers in the fiber aggregate are constrained in the longitudinal direction, the fiber aggregate is high in the rate of variation of phase in the lateral direction, and the fiber aggregate changes readily (moves readily) in response to a strain due to a movement of a wearer. On the other hand, that the degree of freedom is low means that since a large portion of the fibers in the fiber aggregate are constrained in nonspecific directions, the fiber aggregate is low in the rate of variation of phase and does not vary readily (does not move readily) in response to strain.

(5) The interlabial pad according to any one of (1) to (3), wherein the interlabial pad is equipped with a fiber aggregate on the face that contacts the body during fitting; and in the fiber aggregate, the bendability of respective fibers that form the vestibular floor contacting region is adjusted to be higher than the bendability of the fibers that form the inner wall contacting region.

With the present invention of (5), by making the bendability of the fibers in the vestibular floor contacting region high, the degree of freedom of the vestibular floor contacting region can be adjusted. Also, by the respective fibers becoming oriented in the lateral direction of the interlabial pad, movements of the left and right labia of a wearer can be followed more readily. The contacting of the interlabial pad is thus improved further and the falling-off of the interlabial pad from the labia of a wearer due to movements of the wearer can be prevented.

Here, "bendability" refers to the ease of bending or ease of straining of the fibers. That the bendability is high thus means that bending occurs readily and straining occurs readily.

Fibers of high bendability and methods of improving the bendability shall now be described.

As fibers of high bendability, fibers of long fiber length, fibers of small fiber diameter, fibers of low molecular orientation, fibers having titanium oxide or other filler mixed in the fibers, etc., can be cited. Also, though as methods of improving the bendability, embossing and slitting methods can be cited, slitting is not preferable since when slitting is applied to a surface side sheet, the fibers become frayed from the end faces of the slits and fibers may thus become retained on the inner labial walls. Though examples of an emboss pattern are not restricted in particular and include dot-form, wave-form, lattice-form, and other patterns, it is preferable for line-form emboss patterns, directed in the lateral direction, to be provided in a staggered manner so that the fibers will bend readily in the longitudinal direction.

(6) The interlabial pad according to any one of (1) to (3), wherein the interlabial pad is equipped with a fiber aggregate on the face that contacts the body during fitting; and in the fiber aggregate, a part or all of respective fibers that form the vestibular floor contacting region have a higher ductility than the fibers that form the inner wall contacting region.

With the present invention of (6), by making the ductility of the fiber aggregate of the vestibular floor contacting region higher than the ductility of the inner wall contacting region, the vestibular floor contacting region is made to follow movements of the left and right labia of wearer more readily. The tensile strength in the extended (5% strained) state of the fiber aggregate at the vestibular floor contacting region should be no less than 40 cN/inch and no more than 1000 cN/inch.

Here, that the "ductility is high" means that the fibers themselves can extend readily. Fibers can thus slide readily with respect to each other. Methods of increasing the ductility of fibers shall now be described specifically.

First, as examples of fibers of high ductility, fibers of high crimp percentage, fibers, which have been improved in extensibility by the mixing in of a rubber component, split fibers, fibers of low molecular orientation, etc., can be cited. Fiber aggregates, with which the ductility of fibers with respect to each other has been increased by the mixing in of a lubricant, fibers, with which the area of contact of fibers with each other has been reduced by making mutually adjacent fibers different in cross-sectional shape, etc., can also be cited.

As a specific method, wave-form engagement embossing, directed in the longitudinal direction for increasing the ductility in the longitudinal direction, can be cited, and with this method, the extensibility can be controlled by the size and pitch of the wave-like forms. Here, the extensibility is measured as the proportion by which the total width of a sheet extends with respect to the original sheet width. The waviness condition for the vestibular floor contacting region is to provide an engagement pattern with a height of 1.12 mm and a pitch of 2 mm. The extensibility in this case will be 1.5 times. The waviness condition for the inner wall contacting region is to provide an engagement pattern with a height of 0.66 mm and pitch of 2 mm. Though the extensibility in this case will be 1.2 times, the wavy processing does not have to be applied to the inner wall contacting region.

Yet another example shall be described. The total dimension in the longitudinal direction or lateral direction of the surface side sheet is greater than the total dimension in the longitudinal direction or lateral direction of the back face side sheet, and the amount by which the total dimension of the surface side sheet is greater is incorporated in the vestibular floor contacting region. Specifically, wave-like deflections are provided in the vestibular floor contacting region of the surface side sheet. Since the vestibular floor contacting region strains readily due to these deflections (since the deflections can extend), the inner wall contacting region can slide back and forth accompanied by walking movements of a wearer. The deflections may be of the longitudinal direction or the lateral direction. Also, though the deflections may be provided at parts or may be provided in a continuous manner, they are preferably provided in a continuous manner to enable deflection to occur readily.

(7) The interlabial pad according to any one of (1) to (3), wherein the interlabial pad is equipped with a fiber aggregate on the face that contacts the body during fitting; and in the fiber aggregate, a part or all of respective fibers that form the vestibular floor contacting region are higher in at least two among the degree of freedom, bendability, and ductility than the fibers that form the inner wall contacting region.

With the present invention of (7), by the respective fibers that form the vestibular floor contacting region being higher in at least two among the degree of freedom, bendability, and ductility than the inner wall contacting region in the fiber aggregate, the vestibular floor contacting region is made to follow movements of the left and right labia of wearer even more readily.

(8) The interlabial pad according to any one of (1) to (3), wherein the interlabial pad is equipped with a fiber aggregate on the face that contacts the body during fitting; and in the fiber aggregate, the deformability of the shapes of the spaces between the fibers forming the vestibular floor contacting region is higher than the deformability of the shapes of the spaces between the fibers forming the inner wall contacting region.

With the present invention of (8), by the deformability of the shapes of the spaces between the fibers forming the vestibular floor contacting region being higher than the deformability of the shapes of the spaces between the fibers forming the inner wall contacting region in the fiber aggregate, the vestibular floor contacting region can follow movements of the left and right labia of a wearer even more readily. Here, that "spaces between fibers vary" means that the spaces between fibers vary due to movement of the individual fibers. Thus, if the individual fibers can move readily, the variation rate of the spaces will also be large.

(9) The interlabial pad according to any one of (1) to (8), wherein the interlabial pad is fitted upon being folded in two along a longitudinal central line thereof as an axis and comprises a surface side sheet, contacting the body in the fitted state, and a back face side sheet, positioned at the side opposite the side of the surface side sheet, the total dimension in the lateral direction of the surface side sheet and the total dimension in the lateral direction of the back face side sheet are practically the same in a flat plate-like state prior to folding, and when the interlabial pad is folded in two, the surface side sheet is drawn along the direction of folding.

With the present invention of (9), by the total dimension in the lateral direction of the surface side sheet being made practically the same as the total dimension in the lateral direction of the back face side sheet in the flat plate-like state prior to folding, when the interlabial pad is folded in two, the surface side sheet is pulled. Since points of mutual entanglement of fibers, which are provided in advance, are thus loosened once, the fibers become able to slide readily with respect to each other. At the same time, by the spreading of the distances among fibers, spaces, in which the fibers can move, expand. As a result, the surface area of the surface side sheet becomes larger than the back face side sheet and, for example, at the vestibular floor contacting region, the density decreases and the thickness of the surface side sheet becomes thin. Also, at the inner wall contacting region, the density increases and the thickness of the surface side sheet becomes thick. The vestibular floor region, of low density and thin thickness, can thus follow movements of a wearer. Though by the drawing of the surface side sheet, the surface area increases by an amount corresponding to the pulled amount, the density will not necessarily become low. For example, since by the drawing, the points of mutual entanglement of fibers are loosened once, the fibers become oriented in the lateral direction, and thus even if there is no change in the density of the surface side sheet, the vestibular floor contacting region can follow movements of the wearer.

Here with this invention, "to be drawn" means that the surface side sheet is pulled and becomes large in surface area so that portions of low density form at parts.

(10) The interlabial pad according to any one of (1) to (9), wherein the interlabial pad is used for absorbing vaginal discharge or for urinary incontinence.

With the present invention of (10), the interlabial pad of (10) can be used for absorbing vaginal discharge and/or for urinary continence. That is, since the interlabial pad is used upon being sandwiched between the labia, it can be used to absorb secreted material, besides menstrual blood, from the ostium vaginae. Also, since not only the ostium vaginae but the urethral meatus is also positioned between the labia, urine can be absorbed as well.

(11) A method for adjusting a property of an interlabial pad, fitted on by being sandwiched partially or wholly between labia; wherein the interlabial pad comprises an inner wall contacting region contacting the inner walls of the labia of a wearer in a fitted state, and a vestibular floor contacting region contacting the vestibular floor of the wearer in the fitted state; and wherein a method of adjusting the interlabial pad's property of following movements of the wearer, whereby the deformability of the vestibular floor contacting region and the deformability of the inner wall contacting region are differed.

With the present invention of (11), an interlabial pad, which can be improved in the property of following deformations of the interior of the labial that accompany movements of a wearer, can be provided by a method in which the distribution of fibers are differed at parts of the interlabial pad.

As described above, this invention provides an interlabial pad, with which anisotropy is provided in regard to the degree of freedom of the fiber aggregate that forms the face that contacts the labia of a wearer. That is, the region of the interlabial pad that contacts a wearer's vestibular floor and the region that contact inner labial walls are varied in the degree of freedom of the fiber aggregate. An interlabial pad, which provides fitting comfort and safety without making a wearer feel a foreign object sensation, can thus be provided.

DESCRIPTION OF THE PREFERRED EMBODIMENT

The present invention shall now be described more specifically. In the following description of this invention's embodiments, the same components shall be provided with the same symbols and description thereof shall be omitted or simplified.

First Embodiment

<Basic Structure>

First, the basic overall structure of this invention's interlabial pad shall be described.

Figure 1:
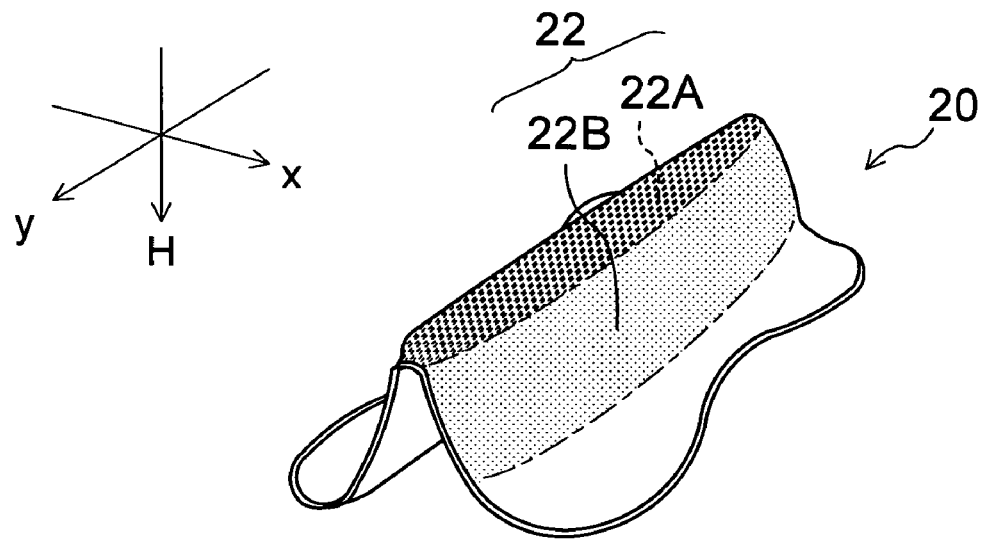
FIG. 1 is a perspective front view showing an interlabial pad of a first embodiment of this invention.

As shown in FIG. 1, this embodiment's interlabial pad (referred to hereinafter as "pad") 20 has an elongate shape, that is, a substantially gourd-like shape with the major diameter along the Y-axis and the minor diameter along the X-axis as viewed from directly above. However, this shape may be elliptical, gourd-like, teardrop-like, etc., and is not restricted in particular as long as it is a shape that fits the labia of women and changes in shape during fitting. Furthermore, though the pad 20 of this embodiment is of a type that is used upon being folded in two along a longitudinal central line as the folding axis, the present invention is not restricted to this type. Pad 20 comprises a long fiber aggregate 22. This fiber aggregate 22 is equipped with a vestibular floor contacting region 22A and an inner wall contacting region 22B. The lateral direction width of the vestibular floor contacting region 22A is approximately 10 mm. Also, the basis weight of the fibers that form the vestibular floor contacting region 22A in this embodiment is 150 g/m$^2$ to 300 g/m$^2$, the basis weight of the fibers that form the inner wall contacting region 22B in this embodiment is 200 g/m$^2$ to 500 g/m$^2$, the embossed area percentage of the vestibular floor contacting region 22A is in the range of 0 to 10%, and the embossed area percentage of the inner wall contacting region 22B is in the range of 0.3 to 40%.

Figure 2:
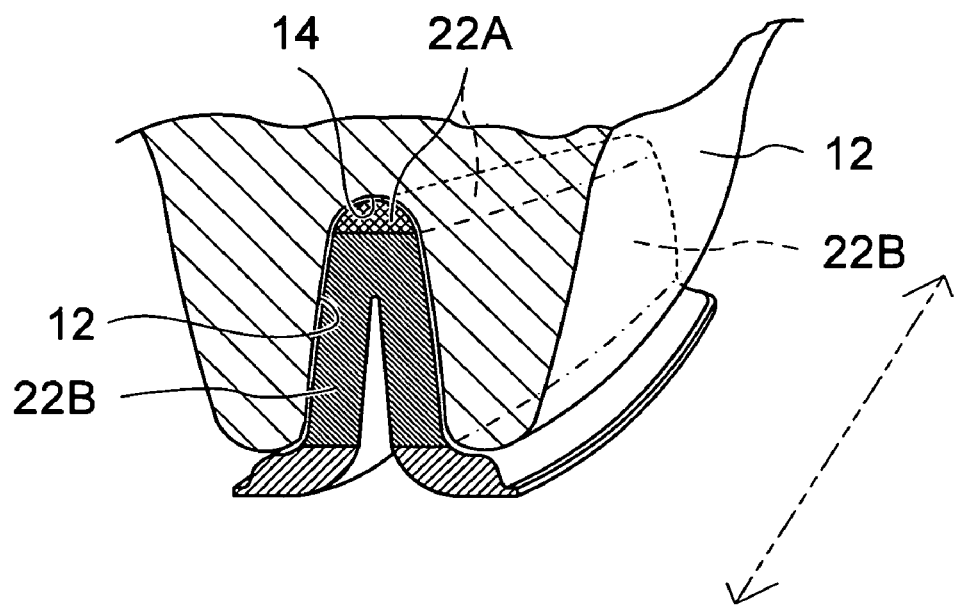
FIG. 2 is a perspective front view showing the interlabial pad of the first embodiment of this invention in the fitted state.
Figure 3:
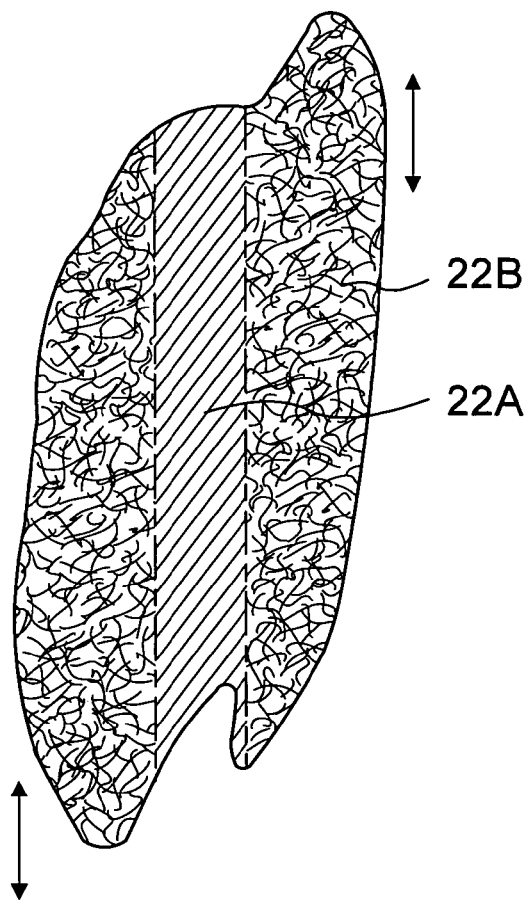
FIG. 3 is a plan view showing the interlabial pad of the first embodiment of this invention

FIG. 2 is a diagram illustrating movements of labia 12 in accordance with movements of a wearer and the actions of vestibular floor contacting region 22A and inner wall contacting region 22B that follow the labial movements. As movements of the left and right labia 12 in accordance with the movements (for example, walking movements) of a wearer, the left and right labia 12 mainly move largely in the direction of an arrow in the figure in accordance with the movements of the legs of the wearer. On the other hand, the movements of the vestibular floor 14 are not as large as the movements of the labia 12. Thus the pad 20 will follow the movements of the labia 12 more readily if the vestibular floor contacting region 22A, which is not so large in friction with the vestibular floor 14, is high in the degree of freedom, and the inner wall contacting region 22B, which is large in friction with the labia 12, is low in the degree of freedom as shown in FIG. 3.

Also with this invention, "tensile strength" is used as a measure for indicating the degrees of freedom of the vestibular floor contacting region 22A and the inner wall contacting region 22B. As a specific measurement method, the tensile strength is measured on a sample of 100 mm length at a pulling rate of 100 mm/min using a tensile tester (made by Instron Japan Co., Ltd.) under a temperature of 25° C. and a humidity of 60%.

The specific arrangement of the fiber aggregate 22 shall now be described.

Figure 4:
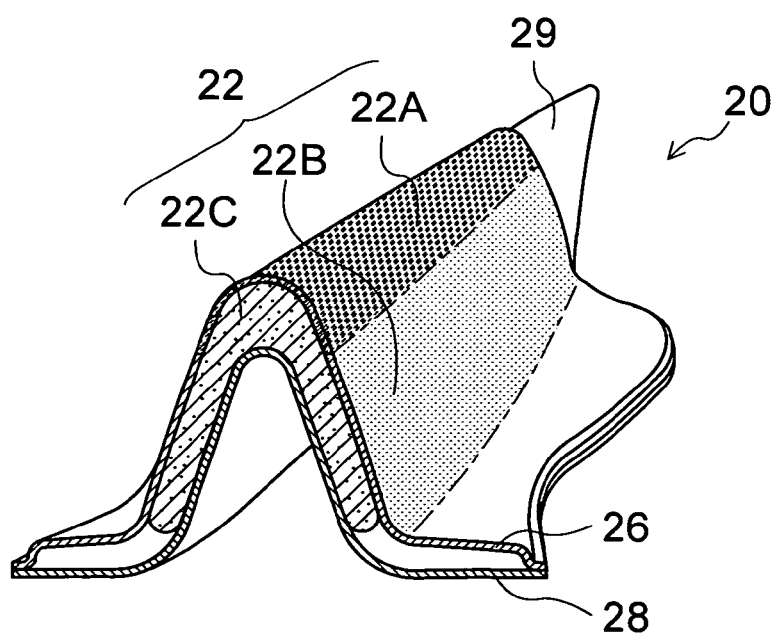
FIG. 4 is a perspective front view showing the interlabial pad of the first embodiment of this invention.

As shown in FIG. 4, the fiber aggregate 22, which is the part of the pad 20 that is contained between the labia in the fitted state, is provided with an absorbent body 22C and preferably a surface side sheet 26 and a back face side sheet 28 are provided above and below the absorbent body. With present embodiment, the absorbent body 22C and the parts of the surface side sheet 26 and the back face side sheet 28 that make up the absorbent body 22C shall be referred to collectively as the fiber aggregate 22, and the fiber aggregate 22 and the parts of the surface side sheet 26 and the back face side sheet that do not cover the absorbent body 22C shall be referred to collectively as the pad 20.

The raw material of the surface side sheet 26 is not restricted in particular as long as it is liquid-permeable and allows the permeation of body fluids of a wearer, and the raw material of the back face side sheet 28 is not restricted in particular as long as it is liquid-impermeable and practically does not allow the permeation of body fluids of a wearer. Also, a part of the pad 20 may have regions that are exposed from the labia. Since the depth of the labia is 14 mm on the average, approximately 14 mm of the pad along an axis H in FIG. 1 that extends perpendicularly from the longitudinal central axis of the absorbent body 22C, which contacts a wearer's vestibular floor during fitting, is not exposed from the labia. The length of the labia is 55 mm on the average and is 50 mm long in front of the ostium vaginae and 5 mm long to the rear of the ostium vaginae. Thus the regions that are exposed from the labia in the longitudinal direction are the region that extends forward beyond 50 mm to the front of the ostium vaginae and the region that extends rearward beyond 5 mm to the rear of the ostium vaginae.

The surface side sheet 26 and the back face side sheet 28 enclose the absorbent body 22C. Though end parts of the absorbent body 22C may be sandwiched by and joined to these sheets, these end parts are preferably not sandwiched by and joined to the sheets. Also, at the end parts at one side (the parts toward the front as viewed from a wearer) in the longitudinal direction of the surface side sheet 26 and the back face side sheet 28, knobs 29, which extend in an elongated manner to enable being picked up readily, may be provided. These knobs 29 are preferably approximately 20 mm in length.

The absorbent body 22C is formed using pulp, chemical pulp, rayon, acetate, natural cotton, polymer absorbent body, or synthetic fibers, etc., in solitary form or as a mixture and is preferably bulky, lasting in form, and low in chemical irritability. Also, this absorbent body 22C may have a two-layer structure. For example, rayon with a fineness of 1.1 to 6.6 dtex and fiber length of 20 to 51 mm may be layered at a basis weight 180 g/m$^2$ at an upper layer that contacts the surface side sheet 26, and pulp may be layered at 80 g/m$^2$ at the region of a lower layer that is to be contained between the labia. In regard to the method of preparing the absorbent body 22C, a sheet, formed by the air laid method; melt blown method, spun lacing method, papermaking method, etc., may be used upon embossing by passing between rolls of dot-form, lattice-form, etc. In this case, the embossed area percentage is preferably within the range of 0 to 20% in the regions that are exposed from the labia and preferably within the range of 0.3 to 40% in the region that is contained between the labia. Also, the absorbent body 22C is subject to linear embossing in order to make it bend and be compressed readily.

For the surface side sheet 26, a raw material that is water-permeable, liquid-compatible, and does not irritate the skin is used. A single type of non-woven fabric obtained by melt blowing, spun bonding, point bonding, or other manufacturing method or a composite material of such fabrics can be cited as examples of such a raw material. Among such materials, an arrangement, having at least cellulose-based, liquid-compatible fibers as the principle component, is preferable in consideration of the compatibility with the inner labial walls so that a wearer will not feel a foreign object sensation due to deviation of the interlabial pad with respect to the inner labial walls. Specifically, a spun-lace non-woven fabric, prepared by mixing 5 to 30% natural cotton with 70 to 95% rayon or acetate, adjusting the basis weight of the mixed fibers to within the range of 20 to 50 g/m$^2$, entangling the fibers with each other by hydroentanglement, and then drying and adjusting the thickness to within the range of 0.3 to 1.0 mm, is preferable. In regard to the quality of the fibers to be used, natural cotton of a fiber length in the range of 15 to 60 mm and rayon or acetate of a fiber length in the range of 25 to 51 mm and a fineness in the range of 1.1 to 6.6 dtex are selected.

With an example in which the surface side sheet 26 is an open pore film, it is preferable for the open pore diameter to be in the range of 0.2 to 5 mm, the pitch to be in the range of 0.2 to 10 mm, and the open pore area percentage to be in the range of 10 to 50% in the vestibular floor contacting region 22A. With regard to the method of manufacture, a so-called PFW may be formed by passing a film through a patterned ram, with which the pore-opening conditions are varied, and then opening pores by applying suction to the film, or open pores may be added further by performing pin embossing on the vestibular floor contacting region 22A of a PFW with uniform open pore conditions. The alignment of the open pores may be staggered, lattice-like, wave-like, etc., and is not restricted in particular. Also, the pore shape may be circular, elliptical, rectangular, etc. Valves may also be formed in the surroundings of the open pore parts. In this case, in order to make it difficult for the open pores to become closed by the valves even when an external pressure is applied, the height of the valves of the open pore parts of the vestibular floor contacting region 22A that contacts the ostium vaginae in particular is preferably made lower than the height of the valves of the inner wall contacting region 22B.

Another example shall be described. In this example, the total dimension in the longitudinal direction or lateral direction of the surface side sheet 26 is greater than the total dimension in the longitudinal direction or lateral direction of the back face side sheet 28, and the amount by which the total dimension of the surface side sheet 26 is greater is incorporated in the vestibular floor contacting region 22A. Specifically, wave-like deflections are provided in the vestibular floor contacting region 22A of the surface side sheet 26. Since the vestibular floor contacting region 22A strains readily due to these deflections (since the deflections can extend), the inner wall contacting region 22B can slide back and forth accompanied by walking movements of a wearer. The deflections may be of the longitudinal direction or the lateral direction. Also, though the deflections may be provided at parts or may be provided in a continuous manner, they are preferably provided in a continuous manner to enable deflection to occur readily.

As yet another example, an example, wherein an emboss that enables extension in the longitudinal direction is applied to the vestibular floor contacting region 22A of the surface side sheet 26, can be cited. An uneven engagement emboss, directed in the longitudinal direction, is applied to the vestibular floor contacting region 22A of a surface side sheet with a basis weight of 15 to 50 g/m$^2$. In regard to specific conditions, by providing an engagement pattern with a height of 1.12 mm and a pitch of 2 mm, the extensibility can be increased by 1.5 times.

As back face side sheet 28, a sheet, which can prevent the menstrual blood that is held in the absorbent body from leaking out of the interlabial pad, can be used. Also, by using a moisture-permeable material, mustiness during fitting can be alleviated and discomfort during fitting can thus be lightened. As such a material, an air-permeable film, obtained by filling with an inorganic filler and performing a drawing process, or an air-permeable, liquid-blocking sheet, having open pores with a pore diameter in the range of 0.1 to 0.6 mm at a porosity of 10 to 30% and being obtained by positioning capillary tubes so as to be directed towards the absorbent body 22C, etc., may be used.

A non-woven fabric may also be used in the back face side sheet 28. Spun-bonded non-woven fabrics, point-bonded non-woven fabrics, through-air non-woven fabrics, etc., can be cited as examples of non-woven fabrics, and these may be subject to a water-repellent treatment. Among these, a non-woven fabric with a three-layer, spun-bonded/melt-blown/spun-bonded (SMS) arrangement, which is formed of ultrafine fibers and includes a melt-blown layer of extremely small interfiber distance, is preferable. In this case, the layers are preferably arranged to have basis weights in the ranges of 5 to 15 g/m$^2$, 1 to 10 g/m$^2$, and 5 to 10 g/m$^2$, respectively.

Second Embodiment

This embodiment's interlabial pad has intermittent parts provided in the vestibular floor contacting region of the fiber aggregate.

Figure 5:
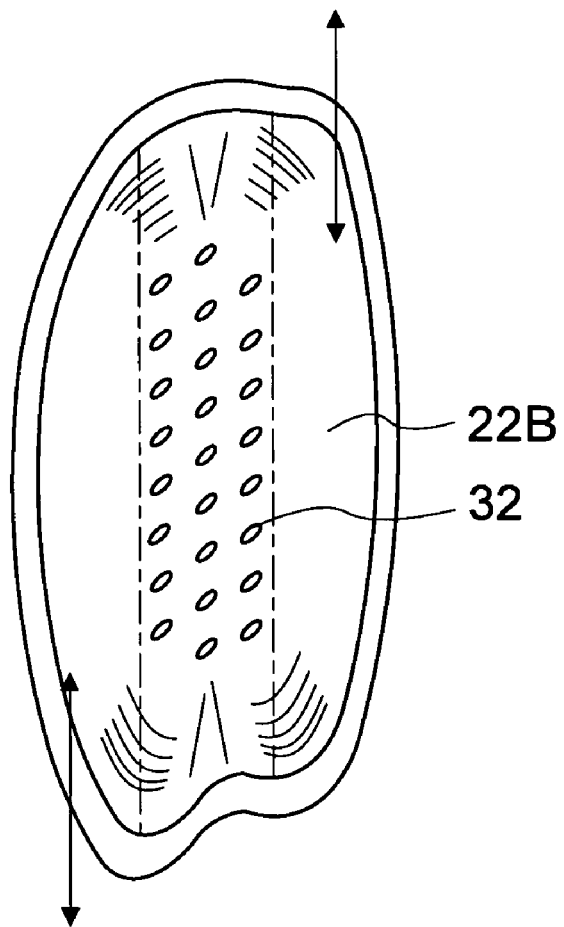
FIG. 5 is a plan view showing an interlabial pad of a second embodiment of this invention.

"Intermittent parts" refer-to slits, open pore parts, and other parts that can deform in shape. As shown in FIG. 5, intermittent parts 32 are provided in the surface side sheet, these intermittent parts 32 follow movements of the left and right labia of a wearer, and in accompaniment, the inner wall contacting region 22B is also enabled to follow the movements. The intermittent parts 32 are preferably 1 mm to 2 mm in dimension. Also, the mutual interval between intermittent parts is preferably 1 mm to 10 mm. The intermittent parts preferably have a size with which the body fluids that have been absorbed will not flow back and more preferably have valves that prevent the body fluids from returning to the face that is in contact with the body and the face at the opposite side.

Third Embodiment

With the interlabial pad of this embodiment, when the pad is folded in two, the surface side sheet is pulled and becomes thin in thickness.

The pad of this embodiment is fitted on upon being folded in two, and in regard to the folding of the pad, the pad may be folded in two in advance in the production line or a wearer may fold the pad in two in the process of fitting. However, in the case where the wearer folds the pad in two, since the fingers of the wearer come in contact with the surface side sheet and this is not preferable in terms of sanitation, it is preferable for the pad to be folded in two in advance in the production line.

Figure 6:
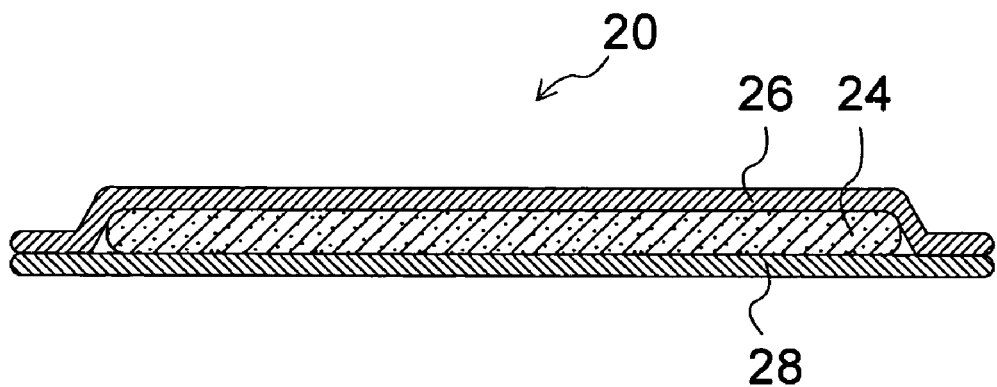
FIG. 6 is a sectional view showing an interlabial pad of a third embodiment of this invention.

FIG. 6 shows the pad 20 prior to being folded in two. The change of density of the surface side sheet when the pad is folded depends largely on the thickness of the absorbent body 22C prior to folding. Prior-art interlabial pads include those with which the surface side sheet 26 is larger than the back face side sheet 28, those with which the back face side sheet 28 is sagged and formed to a pinching part for fitting on the pad 20, etc., and in all cases, the density of the surface side sheet 26 cannot be changed. However, with the present embodiment, since the surface side sheet 26 is pulled in the folding process, a density change occurs. For this, the lateral dimension L1 of the surface side sheet 26 and the lateral dimension L2 of the back face side sheet 28 must be practically the same.

Figure 7:
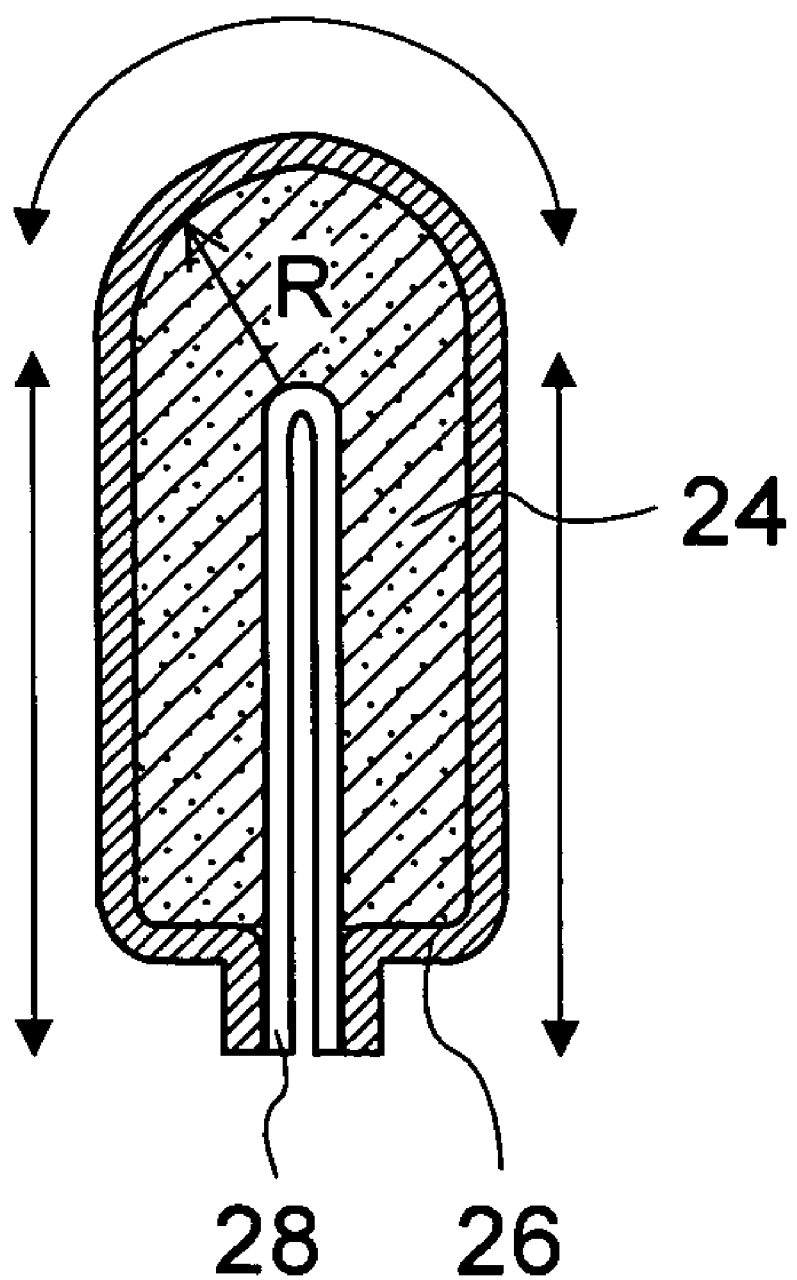
FIG. 7 is a sectional view showing the interlabial pad of the third embodiment of this invention.

FIG. 7 shows the state in which the pad 20 is folded in two. The surface side sheet 26 is pulled across the longitudinal central axis of the pad 20 by a length corresponding to πR, with R being the thickness of the absorbent body 22. The thickness of the part of the surface side sheet 26 forming the vestibular floor contacting region 22A is thus made thinner than the part forming the inner wall contacting region 22B. The vestibular floor contacting region, which is made low in density and thin in thickness, is thus increased in the degree of freedom and is thereby enabled to follow movements of a wearer. The tensile strength in the 5% extended state, which indicates the tensile strength in the lateral direction of the surface side sheet 26 in the state prior to being folded in two, is preferably in the range of 40 to 1000 cN/inch. This is because if the tensile strength is less than 40 cN/inch, even the inner wall contacting region will be readily extendable, while if the tensile strength is greater than 1000 cN/inch, the vestibular floor contacting region will not extend readily.

What is claimed is:

1. An interlabial pad having a longitudinal direction and a lateral direction, the interlabial pad comprising:
   a vestibular floor contacting region consisting of a first fiber aggregate for contacting a vestibular floor of a wearer, the vestibular floor contacting region straddling a central axis in the longitudinal direction and extending over a range of between 5 mm and 25 mm in the lateral direction, and
   a pair of inner wall contacting regions respectively positioned at side portions of the interlabial pad and each consisting of a second fiber aggregate, the side portions being positioned adjacent to laterally opposing sides of the vestibular floor contacting region and having external sides for contacting internal walls of the wearer's labia,
   wherein the interlabial pad has a substantially elongated shape, is worn by being folded in two along a folding axis on the central axis in the longitudinal direction, and each of the pair of inner wall contacting regions includes a non-skin contacting face that is capable of making contact with the other non-skin contacting face when the interlabial pad is folded,
   wherein the vestibular floor contacting region is more easily deformable than each inner wall contacting region, such that the inner wall contacting region is capable of following a shape variation of the labia interior that occurs with the movement of the wearer,
   wherein the tensile strength of a face of the vestibular floor contacting region consisting of the first fiber aggregate that is in contact with the wearer when the interlabial pad is worn, in a state of 5% extension in said longitudinal direction, is no less than 40 cN/inch and no more than 1000 cN/inch, and
   wherein the tensile strength of a face of each inner wall contacting region consisting of the second fiber aggregate that is in contact with the wearer when the interlabial pad is worn, in the state of 5% extension in said longitudinal direction, is no less than 40 cN/inch and no more than 1500 cN/inch.

2. The interlabial pad according to claim 1, wherein the surface side sheet comprises a fiber aggregate; and
   in the fiber aggregate, a degree of freedom of respective fibers that form the vestibular floor contacting region is adjusted to be higher than the degree of freedom of the fibers that form the inner wall contacting region.

3. The interlabial pad according to claim 1, wherein the surface side sheet comprises a fiber aggregate; and
   in the fiber aggregate, the bendability of respective fibers that form the vestibular floor contacting region is adjusted to be higher than the bendability of the fibers that form the inner wall contacting region.

4. The interlabial pad according to claim 1, wherein the surface side sheet comprises a fiber aggregate; and
   in the fiber aggregate, a part or all of respective fibers that form the vestibular floor contacting region have a higher ductility than the fibers that form the inner wall contacting region.

5. The interlabial pad according to claim 1, wherein the surface side sheet comprises a fiber aggregate; and
   in the fiber aggregate, a part or all of respective fibers that form the vestibular floor contacting region are higher in at least two among the degree of freedom, bendability, and ductility than the fibers that form the inner wall contacting region.

6. The interlabial pad according to claim 1, wherein the surface side sheet comprises a fiber aggregate; and
   in the fiber aggregate, the deformability of the shapes of the spaces between the fibers forming the vestibular floor contacting region is higher than the deformability of the shapes of the spaces between the fibers forming the inner wall contacting region.

7. The interlabial pad according to claim 1, wherein the interlabial pad includes a surface side sheet for contacting the wearer's body when worn, a back face side sheet located on an opposite side to the surface side sheet and comprising the non-skin contacting face, and an absorbent body disposed between the surface side sheet and the back face side sheet, the interlabial pad being fitted to the wearer upon being folded in two along the folding axis on the central axis in the longitudinal direction,
   wherein the total dimension in the lateral direction of the surface side sheet and the total dimension in the lateral direction of the back face side sheet are practically the same in a flat plate-like state prior to folding,
   wherein, when the interlabial pad is folded in two, the surface side sheet is drawn along the direction of folding, and
   wherein the surface side sheet and the back face side sheet are layered to each other.

8. The interlabial pad according to claim 1, wherein the interlabial pad is used for absorbing vaginal discharge or for urinary incontinence.

9. The interlabial pad according to claim 1, wherein the surface side sheet comprises a plurality of openings in said vestibular floor contacting region.

10. The interlabial pad according to claim 1, wherein fibers forming the first fiber aggregate measure higher in at least two of a degree of freedom, a bendability, and ductility than fibers forming second fiber aggregate.

11. The interlabial pad according to claim 1, wherein the interlabial pad includes a surface side sheet for contacting the wearer's body when worn, a back face side sheet located on an opposite side to the surface side sheet and comprising the non-skin contacting face, and an absorbent body disposed directly between the surface side sheet and the back face side sheet, the interlabial pad being fitted to the wearer upon being folded in two along the folding axis on the central axis in the longitudinal direction,
   wherein the total dimension in the lateral direction of the surface side sheet and the total dimension in the lateral direction of the back face side sheet are practically in the same in a flat plate-like state prior to folding, and wherein, when the interlabial pad is folded in two, the surface side sheet is drawn along the direction of folding.

12. An interlabial pad having a longitudinal direction and a lateral direction, the interlabial pad comprising:

a vestibular floor contacting region comprising a first fiber aggregate for contacting a vestibular floor of a wearer, the vestibular floor contacting region straddling a central axis in the longitudinal direction and extending over a range of between 5 mm and 25 mm in the lateral direction, and a pair of inner wall contacting regions respectively positioned at side portions of the interlabial pad and each comprising a second fiber aggregate, the side portions being positioned laterally adjacent at the surface of the interlabial pad to laterally opposing sides of the vestibular floor contacting region and having external sides for contacting internal walls of the wearer's labia, wherein the interlabial pad has a substantially elongated shape, is worn by being folded in two along a folding axis on the central axis in the longitudinal direction, and each of the pair of inner wall contacting regions includes a non-skin contacting face that is capable of making contact with the other non-skin contacting face when the interlabial pad is folded, wherein the vestibular floor contacting region is more easily deformable than each inner wall contacting region, such that the inner wall contacting region is capable of following a shape variation of the labia interior that occurs with the movement of the wearer, wherein the tensile strength of a face of the vestibular floor contacting region comprising the first fiber aggregate that is in contact with the wearer when the interlabial pad is worn, in a state of 5% extension in said longitudinal direction, is no less than 40 cN/inch and no more than 1000 cN/inch, and wherein the tensile strength of a face of each inner wall contacting region comprising the second fiber aggregate that is in contact with the wearer when the interlabial pad is worn, in the state of 5% extension in said longitudinal direction, is no less than 40 cN/inch and no more than 1500 cN/inch.

13. An interlabial pad having a longitudinal direction and a lateral direction, the interlabial pad comprising:

a surface side sheet, a back face side sheet, an absorbent body interposed between the surface side sheet and the back face side sheet, wherein the surface side sheet includes a vestibular floor contacting region and a pair of inner wall contacting regions, wherein the vestibular floor contacting region consists of a first fiber aggregate for contacting a vestibular floor of a wearer, and the pair of inner wall contacting regions is positioned substantially symmetrical with respect to the vestibular floor contacting region and consists of a second fiber aggregate for contacting internal walls of the labia of the wearer, wherein the vestibular floor contacting region is more easily deformable than each inner wall contacting region, such that the inner wall contacting region is capable of following a shape variation of the interior of the labia that occurs with the movement of the wearer, wherein the tensile strength of a face of the vestibular floor contacting region that is in contact with the wearer when the interlabial pad is worn, in a state of 5% extension in the longitudinal direction, is no less than 40 cN/inch and no more than 1000 cN/inch, and wherein the tensile strength of a face of each inner wall contacting region that is in contact with the wearer when the interlabial pad is worn, in the state of 5% extension in the longitudinal direction, is no less than 40 cN/inch and no more than 1500 cN/inch.

14. The interlabial pad according to claim 13, wherein the vestibular floor contacting region straddles a central axis in the longitudinal direction and extends over a range of between 5 mm and 25 mm in the lateral direction.

15. The interlabial pad according to claim 13, wherein the surface side sheet comprises a plurality of openings in the vestibular floor contacting region.

16. The interlabial pad according to claim 13, wherein a degree of freedom of respective fibers that form the first fiber aggregate is adjusted to be higher than a degree of freedom of respective fibers that form the second fiber aggregate.

17. The interlabial pad according to claim 13, wherein the bendability of respective fibers that form the first fiber aggregate is adjusted to be higher than the bendability of respective fibers that form the second fiber aggregate.

18. The interlabial pad according to claim 13, wherein one of a portion and the entirety of respective fibers that form the first fiber aggregate has a higher ductility than respective fibers that form the second fiber aggregate.

19. The interlabial pad according to claim 13, wherein one of a portion and the entirety of respective fibers that form the first fiber aggregate is higher in at least two among the degree of freedom, bendability, and ductility than respective fibers that form the second fiber aggregate.

20. The interlabial pad according to claim 13, wherein the deformability of a shape of a space among fibers forming the first fiber aggregate is higher than the deformability of a shape of a space among fibers forming the second fiber aggregate.

21. The interlabial pad according to claim 13, wherein the total dimension in the lateral direction of the surface side sheet and the total dimension in the lateral direction of the back face side sheet are substantially the same in a flat plate-like state prior to folding, and wherein when the interlabial pad is folded in two, the surface side sheet is drawn along the direction of folding.

22. The interlabial pad according to claim 13, wherein the interlabial pad is used for absorbing vaginal discharge or for urinary incontinence.

* * * * *